United States Patent [19]
Cruz

[11] Patent Number: 5,522,507
[45] Date of Patent: Jun. 4, 1996

[54] KIT FOR ENACTING THE TOOTH FAIRY FABLE

[76] Inventor: Leonard Cruz, P.O. Box 848, Somis, Calif. 93066

[21] Appl. No.: 538,531

[22] Filed: Oct. 3, 1995

[51] Int. Cl.⁶ ................................................. B65D 85/00
[52] U.S. Cl. ......................... 206/575; 206/579; 206/83
[58] Field of Search ................................. 206/575, 579, 206/457, 232, 459.5, 83, 0.8, 0.81

[56] References Cited

U.S. PATENT DOCUMENTS

| | | | |
|---|---|---|---|
| 4,828,114 | 5/1989 | Bardeen | 206/575 |
| 4,923,058 | 5/1990 | Dennison | 206/83 |
| 5,394,989 | 3/1995 | Delson | 206/83 X |

*Primary Examiner*—Jacob K. Ackun
*Attorney, Agent, or Firm*—John J. Posta, Jr.

[57] ABSTRACT

A kit is provided which includes all the items necessary to enact the tooth fairy fable. Moreover, the kit includes a container for those items. Preferably, the container and the items are all marked with a tooth fairy emblem. The items include an electric lamp in the shape of a tooth fairy and preferably made of translucent material with the lamp light source within the body of the lamp. In addition, a string pouch or the like, preferably with a bell attached, is provided for placing a tooth therein and for receiving a coin in exchange for the tooth. A pillow case is also included, preferably with a tooth-receiving front pocket. The items further include a tooth receptacle for permanently retaining one or more teeth, preferably with date markers for the same. The receptacle preferably is in the form of a pair of hinged jaws, with tooth-receiving openings corresponding to the positions of baby teeth in the jaws. The kit also includes a container of dispensable gold-colored powder to indicate the recent presence of the tooth fairy. An instruction booklet on the proper procedure for enacting the tooth fairy fable and a note pad and pencil for communicating with the tooth fairy, as well as a tea set with serving tray, tea cups and tea pitcher may also be provided in the kit. Preferably, the items in the kit are miniaturized for use with and by a child.

9 Claims, 2 Drawing Sheets

INSTRUCTION BOOKLET

KIT FOR ENACTING THE TOOTH FAIRY FABLE

BACKGROUND OF THE INVENTION

1. Field of the Invention

The present invention generally relates to play-acting equipment and more particularly to a kit for realistically enacting the tooth fairy fable.

2. Prior Art

Various types of kits and items have been provided for carrying out plays, games and other types of childhood amusements. One of the most endearing of all fables believed by very young children is the fable of the tooth fairy. The fable says that if a child's tooth is left for the tooth fairy, the tooth fairy will come at night after the child is asleep and exchange the tooth for a coin. In some versions of the fable, the tooth is left but a coin is also left in compensation for the child's loss of the tooth, sometimes a traumatic experience for the child with considerable pain and soreness in the gum area where the tooth has come out.

Children, especially very young children, have come to rely on the tooth fairy fable, because of their inherent fascination with beautiful fairies and the world of make-believe, and also because of the monetary compensation received by the child. Parents have found that this fable is a convenient way of distracting the child from the pain and soreness and the fright encountered when a baby tooth is lost by the child.

Obviously, the more realism that can be instilled when the tooth fairy fable is being relied on by the parent will make the enactment of the fable more enjoyable for both child and parent. Accordingly, there is a need for a kit of items which can be used to increase the realism and effectiveness of the enactment of the tooth fairy fable. Such kit should be simple, durable, inexpensive and effective for its intended purposes. Preferably, it should include an instruction booklet to help parents carry out the enactment of the fable to the best effect.

SUMMARY OF THE INVENTION

The improved kit of the present invention satisfies all the foregoing needs. The kit has all the components, that is, items necessary in order to enact the tooth fairy fable effectively and to retain baby teeth on a permanent basis as momento of childhood.

The kit is simple, inexpensive, attractive, durable, reusable and effective for its intended purposes. The kit is substantially as set forth in the ABSTRACT OF THE DISCLOSURE.

Thus, the kit includes an openable container and a plurality of items releasably disposed therein. Preferably, the container and the items are all marked with the design or emblem of a tooth fairy and may be miniaturized.

The items in the container include an electric lamp in the shape of a tooth fairy. Preferably, the lamp body is translucent and has the lamp light source within the body of the lamp so that the tooth fairy body radiates or glows. The body of the lamp may also be fluoresent so that it glows in the dark. The items further include a string pouch for the baby tooth and a bell connected to the pouch to ring for the tooth fairy.

A pillow case is also included which may have a tooth-receiving pocket therein, preferably on the front thereof. A tooth receptacle is also provided for permanently retaining one or more baby teeth as a momento. The receptacle may include means for marking the date of deposit of each baby tooth therein. Preferably, the receptacle is in the form of a pair of hinged jaws which close over one another and which contain tooth-receiving openings or pockets corresponding to the positions of baby teeth in the jaws.

The kit also includes a container of dispensable gold-colored powder to indicate the recent presence of the tooth fairy. Optionally, but preferably, the kit further contains an instruction booklet explaining how the items are to be used to enact the tooth fairy fable and preferably also includes a passage concerning the tooth fairy fable which can be read to the child.

A note pad with pages addressed to the tooth fairy and writing pencil, preferably with tassels, may also be included in the items in the container, so that the child before going to sleep can ask the tooth fairy for her blessing.

The items in the container may also include a tea set having a serving tray, tea cups and tea pitcher, so that the child can set out tea for the tooth fairy as a hospitality gesture. When the tooth fairy arrives after the child falls asleep the tooth fairy will have tea to drink.

Various other aspects of the kit of the present invention are set forth in the following detailed description and accompanying drawings.

DRAWINGS

Figure 10:
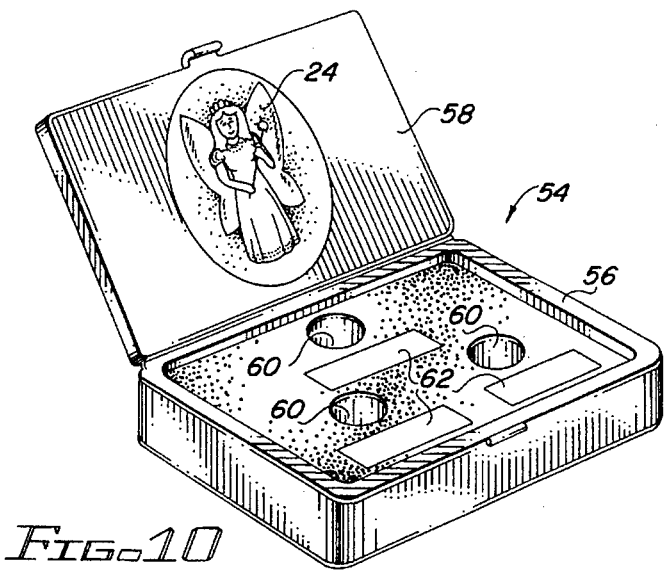
Figure 7:
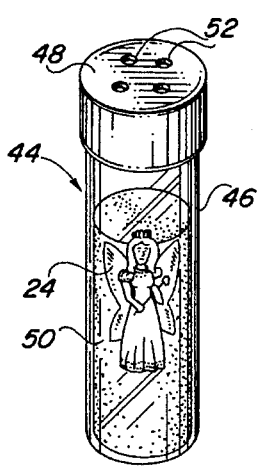
FIG. 7 is a schematic front elevation of a transparent openable container having a dispensable gold-colored powder therein, said container and powder forming items of said kit.
Figure 9:
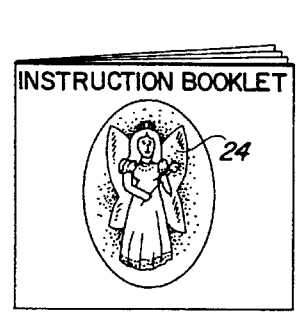
FIG. 9 is a schematic front elevation of an instruction booklet forming part of said kit and containing instructions on how to utilize said items in enacting the tooth fairy fable.
Figure 8A:
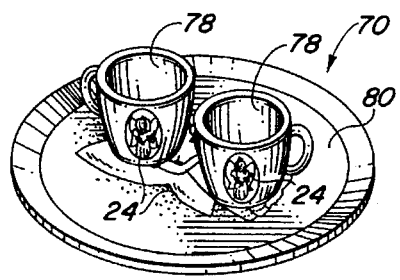
FIG. 8a and 8b are a schematic front perspective view of a miniature tea set forming items of said kit, said set including tea cups, a serving tray and a tea pitcher for offering the tooth fairy a drink.
Figure 8B:
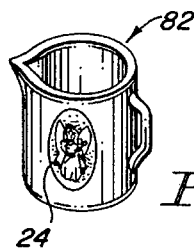
Figure 11:
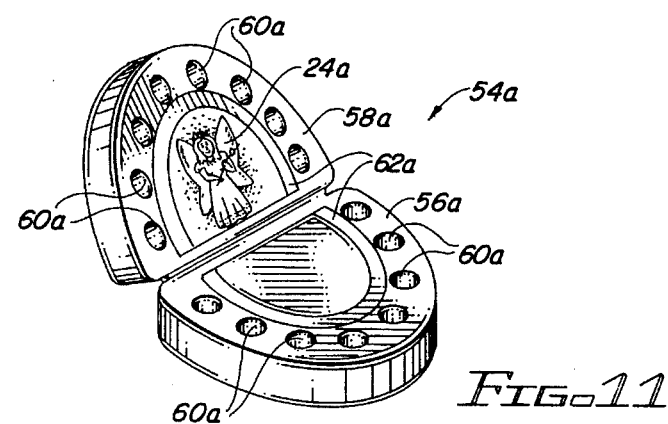

FIG. 10 is a schematic front perspective view of a first preferred embodiment of a receptacle for permanently retaining a plurality of baby teeth and for marking the dates of entry of said teeth in said receptacle; and, FIG. 11 is a schematic top plan view of a second preferred embodiment of the receptacle of the kit of the present invention, said receptacle being in the form of an openable and closeable pair of jaws with pockets therein representing the approximate locations of baby teeth in said jaws.

DETAILED DESCRIPTION

FIGS. 1–10

A preferred embodiment of the improved tooth fairy kit of the present invention is schematically depicted therein. Thus kit 20 is shown which includes an openable container 22 in which are releasably disposed a plurality of items needed in order to effectively enact the tooth fairy fable. Preferably, container 22 and each of the items disposed therein bear the image 24 of a tooth fairy.

Figure 1:
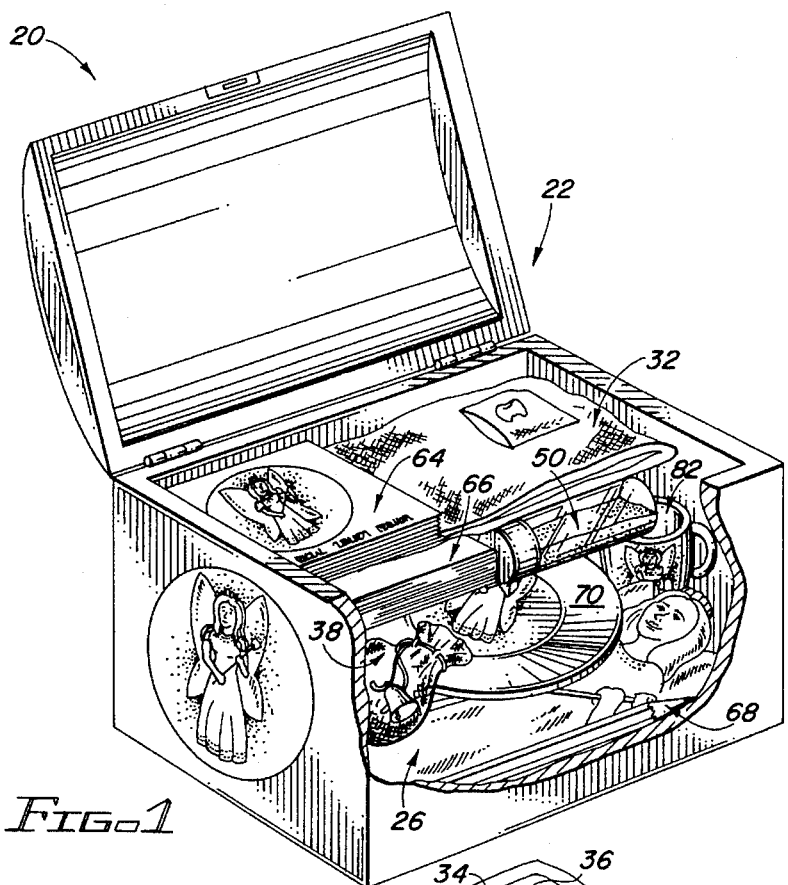
FIG. 1 is a schematic front perspective view, partly broken away, of a preferred embodiment of the improved tooth fairy kit of the present invention, showing various items of the kit in an openable container.
Figure 3:
FIG. 3 is a schematic front elevation of an electric lamp in the form of a translucent body depicting a tooth fairy and with the lamp light source within said body, said lamp being an item of said kit.
Figure 6:
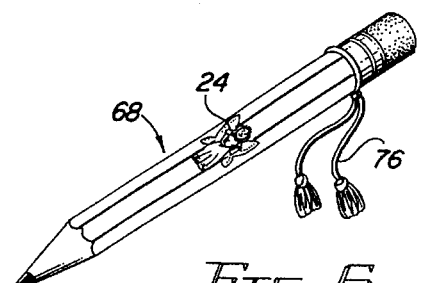
FIG. 6 is a schematic front elevation of a writing pencil bearing tassels and being one of the items of said kit.

The necessary items present in kit 20 include an electric lamp 26 in the shape of a tooth fairy. Preferably, as shown in FIGS. 1 and 3, lamp 26 has a translucent body 28 and a light bulb 30 disposed in said body 28 so that when bulb 30 is electrically powered, lamp body 28 radiates light and glows. Optionally, lamp body 28 may include fluorescent material (not shown), so that it glows at least dimly in the dark without light from bulb 30.

One of the necessary items of kit 20 is a pillow case 32 which preferably contains an openable front pocket 34 for the temporary reception of a baby tooth (not shown). Pockets 34 may be indicated on pillow case by an image 36 of a baby tooth disposed on the front thereof.

Figure 4:
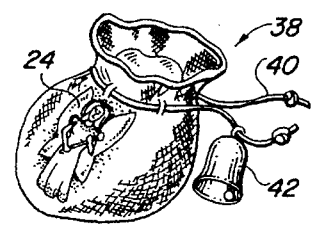
FIG. 4 is a schematic front perspective view of a string pouch forming an item of said kit, said pouch being utilizable as a temporary container for a baby tooth, said pouch also including a tooth fairy-attracting bell attached to the pull string thereof.
Figure 2:
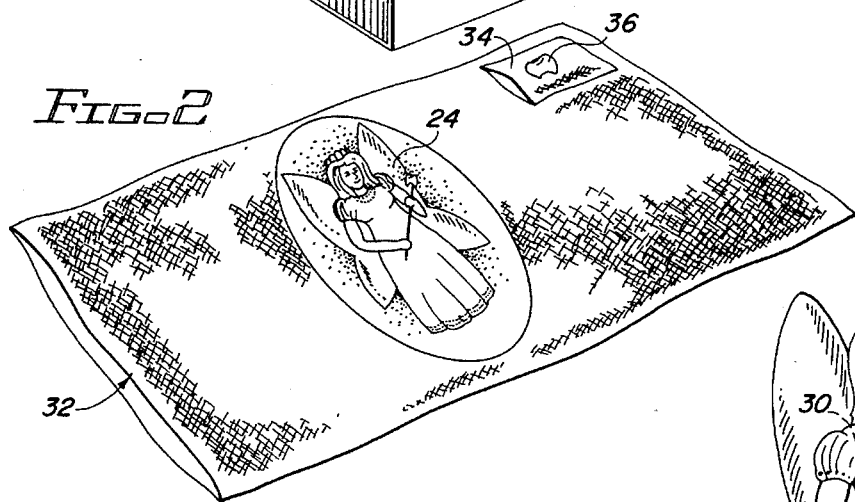
FIG. 2 is a schematic front elevation, partly broken away,of a pillow case which is one of the items of the kit, said pillow case having a front tooth-receiving pocket therein.

As shown in FIG. 4, one of the items of kit 20 is a pouch 38 openable and closeable by a string 40. Pouch 38 may be used in place of pocket 34 for the temporary reception of a baby tooth and/or for placing a coin therein as compensation, by the tooth fairy, for the baby tooth. Preferably, pouch 38 is of leather, cloth or other soft but form-retaining material. A bell 42 may be attached to string 40 for ringing, in order to ostensibly attract the attention of the tooth fairy and indicate the time when a coin is deposited by the tooth fairy in pouch 38.

Kit 20 also includes a container 44 such as a transparent tube 46 with screw top 48, in which is disposed a quantity of gold-colored powder 50, such as gold-colored talc or the like, representing gold dust, and which can be sprinkled about the child's bedroom to indicate the recent visitation of the tooth fairy. If desired, top 48 can have a plurality of openings 52 therein through which powder 50 can be readily dispensed from tube 46.

Kit 20 further includes a receptacle in the form of an openable container 54 having a main body 56 and a hinged lid 58. Body 56 includes a spaced plurality of tooth-receiving pockets 60 for permanent retention of baby teeth. Body 56 may also contain strips 62 or other similar items on which the dates of depositing of baby teeth in pockets 60 can be inscribed.

Optionally, but preferably, kit 20 further includes one or more of the following items: an instruction booklet 64, a note pad 66, a writing pencil 68 and a miniature tea set 70.

Instruction booklet 64 preferably includes indicia which set out information on how to enact the tooth fairy fable by utilizing the items in kit 20. Preferably, booklet 64 also contains a detailed description of the tooth fairy for reading to the child donating a tooth, and may further include other useful information.

Figure 5:
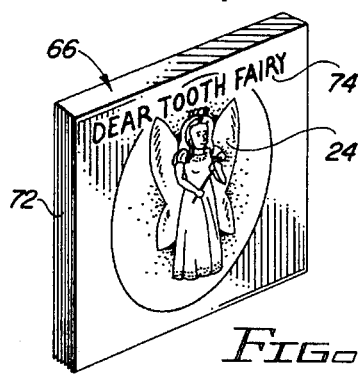
FIG. 5 is a schematic front perspective view of a note pad with the pages thereof addressed to the tooth fairy, the note pad being one of the items of the kit.

Note pad 66 has a plurality of removable pages 72 therein, each of which bears the outline image of the tooth fairy and is addressed to the tooth fairy, as per indicia 74 printed thereon, as shown in FIG. 5. Writing pencil 68 which preferably bears attractive tassels 76 is provided in order for the child to write a note on pad 66 to the tooth fairy, asking for a present (coin) or her blessing.

Tea set 70 is preferably provided in kit 20 to enable the child to offer the tooth fairy hospitality in the form of a cup of tea while the child is asleep. Set 70 may include miniaturized versions of tea cups 78, a serving tray 80 and a tea pitcher 82. With the aid of a parent or guardian, the child can set up pitcher 80 with tea or a simulated tea and pour such liquid out into cups 78 before going to sleep. For full effect, one of cups 78 should be drained of tea while the child is asleep, to simulate the drinking thereof by the tooth fairy.

Kit 20 provides all the necessary items for realistically enacting the tooth fairy fable to the delight of a small child, and for retaining baby teeth as a permanent record of childhood. Kit 20, as indicated above, can also include a number of optional items which further enhance the ability of the parent or guardian to carry out the tooth fairy fable. Kit 20 is inexpensive, durable, efficient, attractive and pleasureable to use.

Kit 20 can be fabricated in full or miniaturized form from suitable conventional materials to provide an appealing means of entertaining a child and taking away the fear and discomfort of the child which may accompany the loss of his or her tooth.

FIG. 11

A second preferred embodiment of the tooth receptacle item in the kit of the present invention is schematically depicted in FIG. 11. Thus, receptacle 54a is shown. Components thereof similar to those of receptacle 54 bear the same numerals but are succeeded by the letter "a". Receptacle 54a can be substituted for receptacle 54 in kit 20, if desired.

Receptacle 54a differs from receptacle 54 only as follows:

a) Lid 58a has a plurality of spaced tooth-retaining pockets 60a therein, rather than merely being a cover, as is lid 58;

b) Receptacle 54a has the configuration of a pair of jaws comprising lid 58a and body 56a hinged together and of equal size and shape, with spaced tooth-retaining pockets 60a therein disposed in the approximate positions of baby teeth in baby jaws; and, c) Strips 62a are disposed as semi-circles on the inner border of the pocket-containing areas of receptacle 54a.

Receptacle 54a has the other advantages of receptacle 54.

Various other modifications, changes, alterations and additions can be made in the improved tooth fairy kit of the present invention, its components and parameters. All such changes, modifications, alterations and additions as are within the scope of the appended claims form part of the present invention.

What is claimed is:

1. An improved kit for enacting the tooth fairy fable, said kit comprising, in combination:

a) an openable container; and, b) releasably disposed in said container items adapted to facilitate the enactment of the tooth fairy fable, said items including:

i.) an electric lamp in the shape of a tooth fairy, ii.) a pillow case bearing the image of a tooth fairy, iii.) a money pouch bearing the image of a tooth fairy, iv.) a receptacle having at least one tooth-retaining pocket, and, v.) a container with an openable lid, said container containing gold-colored powder, to signify the recent presence of the tooth fairy.

2. The improved kit of claim 1 wherein said receptacle includes a plurality of spaced tooth-retaining pockets and means for marking the dates of depositing of teeth in said receptacle.

3. The improved kit of claim 2 wherein said receptacle is in the shape of a pair of jaws with said pockets disposed approximately in the same positions as a set of baby teeth.

4. The improved kit of claim 3 wherein one of said jaws is said lid.

5. The improved kit of claim 1 wherein said kit includes a note pad for writing to the tooth fairy, a pencil for carrying out said writing and an instruction booklet setting forth the procedure for enacting the tooth fairy fable.

6. The improved kit of claim 5 wherein said kit also includes a miniature tea set having a serving tray, tea cups and tea pitcher.

7. The improved kit of claim 6 wherein each of said items bears the image of the tooth fairy, wherein each of the pages of said notebook is addressed to the tooth fairy, wherein said pouch has a bell to attract the tooth fairy and wherein said pencil has tassels to attract the user.

8. The improved kit of claim 7 wherein each of said items and said container are miniaturized for use by and on behalf of children, and wherein said lamp is translucent with the light source for said lamp disposed in the body of said lamp.

9. The improved kit of claim 1 wherein said pillow case has a pocket for placing a tooth therein and for receiving a coin in exchange.

\* \* \* \* \*